(12) United States Patent
Agostini

(10) Patent No.: US 6,593,433 B2
(45) Date of Patent: Jul. 15, 2003

(54) SILOXY CONTAINING SALT COMPOUNDS

(75) Inventor: Giorgio Agostini, Colmar-Berg (LU)

(73) Assignee: The Goodyear Tire & Rubber Company, Akron, OH (US)

( * ) Notice: Subject to any disclaimer, the term of this patent is extended or adjusted under 35 U.S.C. 154(b) by 91 days.

(21) Appl. No.: 09/794,446

(22) Filed: Feb. 27, 2001

(65) Prior Publication Data

US 2002/0010239 A1 Jan. 24, 2002

Related U.S. Application Data

(60) Provisional application No. 60/196,858, filed on Apr. 12, 2000.

(51) Int. Cl.⁷ .................................................. C08F 36/04
(52) U.S. Cl. ................. 525/332.6; 525/332.7; 525/331.9; 524/495; 524/492
(58) Field of Search .................. 525/332.6, 332.7; 524/495, 492

(56) References Cited

U.S. PATENT DOCUMENTS

| | | | | | |
|---|---|---|---|---|---|
| 4,490,500 A | * | 12/1984 | Smith | ........................ | 524/378 |
| 5,159,009 A | * | 10/1992 | Wolff et al. | ................. | 524/495 |
| 5,698,619 A | * | 12/1997 | Cohen et al. | ............... | 524/188 |
| 5,916,973 A | * | 6/1999 | Zimmer et al. | ............. | 525/236 |
| 6,184,306 B1 | * | 2/2001 | Materne et al. | .......... | 525/332.7 |
| 6,340,724 B1 | * | 1/2002 | Gorl et al. | ................... | 524/442 |
| 6,410,625 B1 | * | 6/2002 | Materne et al. | ............. | 524/262 |
| 6,465,670 B2 | * | 10/2002 | Thise et al. | ................. | 556/400 |
| 2002/0010239 A1 | * | 1/2002 | Agostini | ..................... | 524/188 |
| 2002/0022085 A1 | * | 2/2002 | Thise et al. | ................. | 427/215 |

FOREIGN PATENT DOCUMENTS

| EP | 1094067 | 4/2001 | ............. C07F/7/18 |
|---|---|---|---|
| EP | 1 178 077 A1 | * 2/2002 | ............ C08K/9/06 |

OTHER PUBLICATIONS

Great Britain Search Report.

* cited by examiner

*Primary Examiner*—David W. Wu
*Assistant Examiner*—Rip A Lee
(74) *Attorney, Agent, or Firm*—Bruce J. Hendricks; John D. DeLong

(57) ABSTRACT

The present invention relates to siloxy containing salts of the formula:

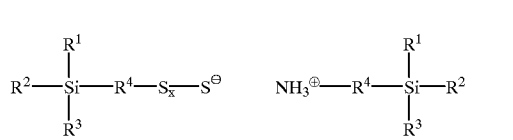

wherein each $R^1$ and $R^2$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes alkyl substituted arylenes having from 6 to 10 carbon atoms, $-R^5-O-R^6-$ and $-R^5-NH-R^7-$; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and x is an integer of from 0 to 7.

16 Claims, No Drawings

SILOXY CONTAINING SALT COMPOUNDS

This application claims the benefit of U.S. Provisional Application No. 60/196,858 filed Apr. 12, 2000.

FIELD OF THE INVENTION

The present invention relates to a compound which is useful in rubber compositions containing fillers and the processing of a rubber composition containing such fillers.

BACKGROUND OF THE INVENTION

U.S. Pat. Nos. 3,842,111, 3,873,489 and 3,978,103 disclose various sulfur containing organosilane compounds. Sulfur containing organosilane compounds are useful coupling agents between rubber and silica fillers providing for improved physical properties. Unfortunately during mixing with rubber, processing problems ensue.

SUMMARY OF THE INVENTION

The present invention relates to siloxy containing salt compounds of the formula:

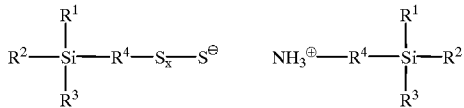

wherein each $R^1$ and $R^2$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes alkyl substituted arylenes having from 6 to 10 carbon atoms, —$R^5$—O—$R^6$— and —$R^5$—NH—$R^7$—; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and x is an integer of from 0 to 7.

DETAILED DESCRIPTION OF THE INVENTION

There is also disclosed a method for processing a rubber composition which comprises mixing
(i) 100 parts by weight of at least one sulfur vulcanizable elastomer containing olefinic unsaturation;
(ii) 10 to 250 phr of a filler; and
(iii) 0.05 to 10 phr of a compound of the formula:

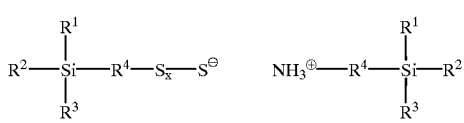

wherein each $R^1$ and $R^2$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes alkyl substituted arylenes having from 6 to 10 carbon atoms, —$R^5$—O—$R^6$— and —$R^5$—NH—$R^7$—; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and x is an integer of from 0 to 7.

There is also disclosed a rubber composition comprising an elastomer containing olefinic unsaturation and a compound of the formula:

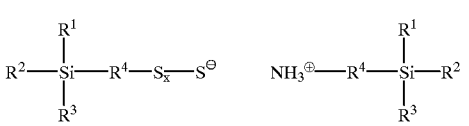

wherein each $R^1$ and $R^2$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes alkyl substituted arylenes having from 6 to 10 carbon atoms, —$R^5$—O—$R^6$— and —$R^5$—NH—$R^7$—; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and x is an integer of from 0 to 7.

The present invention may be used to process rubbers or elastomers containing olefinic unsaturation. The phrase "rubber or elastomer containing olefinic unsaturation" is intended to include both natural rubber and its various raw and reclaim forms as well as various synthetic rubbers. In the description of this invention, the terms "rubber" and "elastomer" may be used interchangeably, unless otherwise prescribed. The terms "rubber composition", "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Specific examples of synthetic rubbers include neoprene (polychloroprene), polybutadiene (including cis- 1,4-polybutadiene), polyisoprene (including cis-1,4-polyisoprene), butyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. Additional examples of rubbers which may be used include silicon-coupled and tin-coupled star-branched polymers. The preferred rubber or elastomers are polybutadiene and SBR.

In one aspect the rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

The relatively high styrene content of about 30 to about 45 for the E-SBR can be considered beneficial for a purpose of enhancing traction, or skid resistance, of the tire tread. The presence of the E-SBR itself is considered beneficial for a purpose of enhancing processability of the uncured elastomer composition mixture, especially in comparison to a utilization of a solution polymerization prepared SBR (S-SBR).

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

A purpose of using S-SBR is for improved tire rolling resistance as a result of lower hysteresis when it is used in a tire tread composition.

The 3,4-polyisoprene rubber (3,4-PI) is considered beneficial for a purpose of enhancing the tire's traction when it is used in a tire tread composition. The 3,4-PI and use thereof is more fully described in U.S. Pat. No. 5,087,668 which is incorporated herein by reference. The Tg refers to the glass transition temperature which can conveniently be determined by a differential scanning calorimeter at a heating rate of 10° C. per minute.

The cis 1,4-polybutadiene rubber (BR) is considered to be beneficial for a purpose of enhancing the tire tread's wear, or treadwear. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The siloxy containing compounds of the present invention are of the formula:

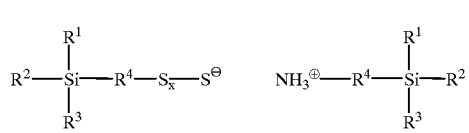

I wherein each $R^1$ and $R^2$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes alkyl substituted arylenes having from 6 to 10 carbon atoms, —$R^5$—O—$R^6$— and —$R^5$—NH—$R^7$—; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and x is an integer of from 0 to 7. Preferably, $R^1$, $R^2$ and $R^3$ are each an alkoxy group having from 1 to 3 carbon atoms, each $R^4$ are alkylenes having 1 to 3 carbon atoms and x is 0.

Representative of the siloxy containing salt compounds of Formula I are ammonium ethyl triethoxysilane ethyl triethoxy silane sulfide, ammonium propyl triethoxysilane propyl triethoxy silane sulfide, ammonium ethyl trimethoxysilane ethyl trimethoxy silane sulfide, ammonium propyl trimethoxysilane propyl trimethoxy silane sulfide; ammonium ethyl triethoxysilane ethyl triethoxy silane disulfide, ammonium propyl triethoxysilane propyl triethoxy silane disulfide, ammonium ethyl trimethoxysilane ethyl trimethoxy silane disulfide, ammonium propyl trimethoxysilane propyl trimethoxy silane disulfide; ammonium ethyl triethoxysilane ethyl triethoxy silane trisulfide, ammonium propyl triethoxysilane propyl triethoxy silane trisulfide, ammonium ethyl trimethoxysilane ethyl trimethoxy silane trisulfide, ammonium propyl trimethoxysilane propyl trimethoxy silane trisulfide; ammonium ethyl triethoxysilane ethyl triethoxy silane tetrasulfide, ammonium propyl triethoxysilane propyl triethoxy silane tetrasulfide, ammonium ethyl trimethoxysilane ethyl trimethoxy silane tetrasulfide, ammonium propyl trimethoxysilane propyl trimethoxy silane tetrasulfide; ammonium ethyl triethoxysilane ethyl triethoxy silane pentasulfide, ammonium propyl triethoxysilane propyl triethoxy silane pentasulfide, ammonium ethyl trimethoxysilane ethyl trimethoxy silane pentasulfide, ammonium propyl trimethoxysilane propyl trimethoxy silane pentasulfide; ammonium ethyl triethoxysilane ethyl triethoxy silane hexasulfide, ammonium propyl triethoxysilane propyl triethoxy silane hexasulfide, ammonium ethyl trimethoxysilane ethyl trimethoxy silane hexasulfide, ammonium propyl trimethoxysilane propyl trimethoxy silane hexasulfide; ammonium ethyl triethoxysilane ethyl triethoxy silane heptasulfide, ammonium propyl triethoxysilane propyl triethoxy silane heptasulfide, ammonium ethyl trimethoxysilane ethyl trimethoxy silane heptasulfide, ammonium propyl trimethoxysilane propyl trimethoxy silane heptasulfide; ammonium ethyl triethoxysilane ethyl triethoxy silane octasulfide, ammonium propyl triethoxysilane propyl triethoxy silane octasulfide, ammonium ethyl trimethoxysilane ethyl trimethoxy silane octasulfide and ammonium propyl trimethoxysilane propyl trimethoxy silane octasulfide.

The siloxy containing salt compounds of formula I when x is 0 may be prepared by reacting a mercaptan compound of the formula:

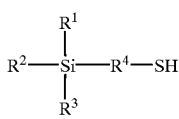

II with an amino compound of the formula:

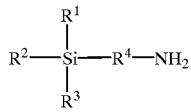

III wherein $R^1$, $R^2$, $R^3$ and $R^4$ are as described above.

The mercaptan compounds of formula II and the amino compounds of formula III are commercially available. Representative examples of compounds of formula II include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl tri-isopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl diethoxy methylsilane, 3-mercaptopropyl ethoxy dimethylslane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; 2-mercaptomethyltolyl trimethoxysilane; 2-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

The amino compounded Formula III are commercially available. Representative examples include 4-aminobutyltriethoxysilane, (aminoethylaminomethyl) phenethyl-trimethoxysilane, N-(2-aminoethyl)-3-aminopropylmethyl-dimethoxysilane, N-(2-aminoethyl)-3-aminopropyltri-methoxysilane; N-(6-aminohexyl) aminopropyl-trimethoxysilane, 3-(m-aminophenoxy) propyltrimethoxy-silane, m-aminophenyltrimethoxysilane, p-aminophenyltrimethoxysilane, 3-(1-aminopropoxy)-3,3-dimethyl-1-propenyltrimethoxysilane, 3-aminopropyldiisopropylethoxy-silane, 3-aminopropyldimethylethoxysilane, 3-aminopropylmethyldiethoxysilane, 3-aminopropyltriethoxysilane, 3-aminopropyltrimethoxysilane, 3-aminopropyltris (methoxyethoxy-ethoxy)silane and 3-aminopropyltris (trimethylsiloxy)-silane.

The molar ratios of the mercaptan compound of Formula II to the amino compound of Formula III may vary. Generally speaking, the molar ratio will range from 1.5:1 to 1:1.5 with a 1:1 ratio being preferred.

The siloxy containing salt compound of formula I when x is an integer of from 1 to 7 may be prepared by reacting the mercaptan of formula II with an amino compound of formula II in the presence of sulfur, such as $S_8$ Rhombic sulfur may be used.

The molar ratio of the sulfur, $S_8$, compound to the mercaptan compound of formula II or the amino compound of formula II may vary. Generally speaking, the molar ratio will range from 0.1:1 to 2:1, with a 1:1 ratio being preferred.

The above reaction is generally conducted in a non-glass reaction vessel. Preferably, the reaction vessel is made of polyethylene and the reaction may be conducted neat or in the presence of a suitable solvent. If a solvent is used, the primary criteria is to use a solvent which does not react with the starting materials or end product. Representative organic solvents include chloroform, dichloromethane, carbon tetrachloride, hexane, heptane, cyclohexane, xylene, benzene, toluene, aliphatic and cycloaliphatic alcohols. Preferably, water is avoided to prevent reaction with the siloxy groups of the compounds.

It has been described and disclosed how to prepare a compound of formula I. In accordance with one embodiment after the compound of formula I has been prepared, it may be thereafter be added to a rubber composition. In accordance with another embodiment, one may prepare the compound of formula I in situ in the rubber, namely, react the mercaptan of formula II with the amino compound of formula III in the presence of rubber to form the compound of formula I. If one desires to prepare the compound of formula 1 when x is 1 to 7, a sulfur compound must be present to accomplish any in-situ preparation.

The siloxy salt containing compound of formula I may be added to the rubber by any conventional technique such as on a mill or in a Banbury. The amount of the siloxy salt compound may vary widely depending on the type of rubber and other compounds present in the rubber. Generally, the amount of the siloxy salt compound is used in a range of from about 0.05 to about 15.0 phr with a range of 0.1 to about 10.0 phr being preferred. The siloxy compound is preferably added in the nonproductive stage with a filler and optional sulfur-containing organosilicon coupling agent.

For ease in handling, the siloxy salt compound may be used per se or may be deposited on suitable carriers.

Examples of carriers which may be used in the present invention include silica, carbon black, alumina, alumina silicates, clay, kieselguhr, cellulose, silica gel and calcium silicate.

The rubber composition should contain a sufficient amount of filler to contribute a reasonably high modulus and high resistance to tear. Preferably, the filler is silica, aluminosilicates, carbon black, and/or modified carbon black. Preferably, the filler is hydrophilic in nature. Conventional fillers may also be present. The filler may be added in amounts ranging from 10 to 250 phr. Preferably, the filler is present in an amount ranging from 15 to 80 phr. The preferred filler is silica. The amount of carbon black, if used, may vary. Generally speaking, the amount of carbon black will vary from 0 to 100 phr. Preferably, the amount of carbon black will range from 0 to 40 phr. It is to be appreciated that the silica coupler may be used in conjunction with a carbon black, namely pre-mixed with a carbon black prior to addition to the rubber composition, and such carbon black is to be included in the aforesaid amount of carbon black for the rubber composition formulation.

The commonly employed siliceous pigments used in rubber compounding applications can be used as the silica in this invention, including pyrogenic and precipitated siliceous pigments (silica) and aluminosilicates, although precipitate silicas are preferred. The siliceous pigments preferably employed in this invention are precipitated silicas such as, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society*, Volume 60, Page 304 (1930).

The silica may also be typically characterized by having a dibutylphthalate (DBP) absorption value in a range of about 100 to about 400, and more usually about 150 to about 300.

Further, the silica, as well as the aforesaid alumina and aluminosilicate may be expected to have a CTAB surface area in a range of about 100 to about 220. The CTAB surface area is the external surface area as evaluated by cetyl trimethylammonium bromide with a pH of 9. The method is described in ASTM D 3849 for set up and evaluation. The CTAB surface area is a well known means for characterization of silica.

Mercury surface area/porosity is the specific surface area determined by Mercury porosimetry. For such technique, mercury is penetrated into the pores of the sample after a thermal treatment to remove volatiles. Set-up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p.39 (1959) or according to DIN 66133. For such an evaluation, a CARLO-ERBA Porosimeter 2000 might be used.

The average mercury porosity specific surface area for the silica should be in a range of about 100 to 300 m²/g.

A suitable pore-size distribution for the silica, alumina and aluminosilicate according to such mercury porosity evaluation is considered herein to be five percent or less of its pores have a diameter of less than about 10 nm; 60 to 90 percent of its pores have a diameter of about 10 to about 100 nm; 10 to 30 percent of its pores have a diameter of about 100 to about 1000 nm; and 5 to 20 percent of its pores have a diameter of greater than about 1000 nm.

The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Z1165MP and Z165GR and silicas available from Degussa AG with, for example, designations VN2, VN3, BV3380GR, etc, and silicas available from Huber, for example Huber Sil 8745.

The siloxy salt containing compound of Formula I may be used as a silica coupling agent. They may be used alone and/or optionally in combination with additional sulfur containing organosilicon compounds. Examples of suitable sulfur containing organosilicon compounds are of the formula:

$$Z\text{-Alk-}S_n\text{-Alk-}Z \qquad \qquad IV$$

in which Z is selected from the group consisting of:

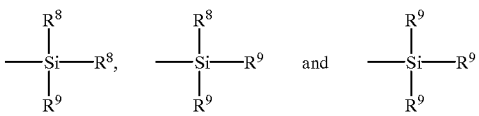

where $R^8$ is an alkyl group of 1 to 4 carbon atoms, cyclohexyl or phenyl; $R^9$ is alkoxy of 1 to 8 carbon atoms, or cycloalkoxy of 5 to 8 carbon atoms; Alk is a divalent hydrocarbon of 1 to 18 carbon atoms and n is an integer of 2 to 8.

Specific examples of sulfur containing organosilicon compounds which may be used in accordance with the present invention include: 3,3'-bis(trimethoxysilylpropyl) disulfide, 3,3'-bis(triethoxysilylpropyl) disulfide, 3,3'-bis(triethoxysilylpropyl) tetrasulfide, 3,3'-bis(triethoxysilylpropyl) octasulfide, 3,3'-bis(trimethoxysilylpropyl) tetrasulfide, 2,2'-bis(triethoxysilylethyl) tetrasulfide, 3,3'-bis(trimethoxysilylpropyl) trisulfide, 3,3'-bis(triethoxysilylpropyl) trisulfide, 3,3'-bis(tributoxysilylpropyl) disulfide, 3,3'-bis(trimethoxysilylpropyl) hexasulfide, 3,3'-bis(trimethoxysilylpropyl) octasulfide, 3,3'-bis(trioctoxysilylpropyl) tetrasulfide, 3,3'-bis(trihexoxysilylpropyl) disulfide, 3,3'-bis(tri-2"-ethylhexoxysilylpropyl) trisulfide, 3,3'-bis(triisooctoxysilylpropyl) tetrasulfide, 3,3'-bis(tri-t-butoxysilylpropyl) disulfide, 2,2'-bis(methoxy diethoxy silyl ethyl) tetrasulfide, 2,2'-bis(tripropoxysilylethyl) pentasulfide, 3,3'-bis(tricyclonexoxysilylpropyl) tetrasulfide, 3,3'-bis(tricyclopentoxysilylpropyl) trisulfide, 2,2'-bis(tri-2"-methylcyclohexoxysilylethyl) tetrasulfide, bis (trimethoxysilylmethyl) tetrasulfide, 3-methoxy ethoxy propoxysilyl 3'-diethoxybutoxy-silylpropyltetrasulfide, 2,2'-bis(dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis (trimethoxysilylbutyl) tetrasulfide, 6,6'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilyl-buten-2-yl) tetrasulfide, 4,4'-bis (trimethoxysilylcyclohexylene) tetrasulfide, 5,5'-bis (dimethoxymethylsilylpentyl) trisulfide, 3,3'-bis (trimethoxysilyl-2-methylpropyl) tetrasulfide, 3,3'-bis (dimethoxyphenylsilyl-2-methylpropyl) disulfide.

The preferred sulfur containing organosilicon compounds are the 3,3'-bis(trimethoxy or triethoxy silylpropyl) sulfides. The most preferred compounds are 3,3'-bis (triethoxysilylpropyl) tetrasulfide and 3,3'-bis (triethoxysilylpropyl) disulfide. Preferably Z is:

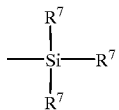

where $R^9$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 2 to 4.

The amount of the above sulfur containing organosilicon compound in a rubber composition may vary. Generally speaking, the amount of the compound of Formula IV will range from 0.5 to 20 phr. Preferably, the amount will range from 1 to 10 phr.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur vulcanized material (rubbers), the additives mentioned above are selected and commonly used in conventional amounts.

Representative examples of sulfur donors include elemental sulfur (free sulfur), an amine disulfide, polymeric polysulfide and sulfur olefin adducts. Preferably, the sulfur vulcanizing agent is elemental sulfur. The sulfur vulcanizing agent may be used in an amount ranging from 0.5 to 8 phr, with a range of from 1.5 to 6 phr being preferred. Typical amounts of tackifier resins, if used, comprise about 0.5 to about 10 phr, usually about 1 to about 5 phr. Typical amounts of processing aids comprise about 1 to about 50 phr. Such processing aids can include, for example, aromatic, naphthenic, and/or paraffinic processing oils. Typical amounts of antioxidants comprise about 1 to about 5 phr.

Representative antioxidants may be, for example, diphenyl-p-phenylenediamine and others, such as, for example, those disclosed in the *Vanderbilt Rubber Handbook* (1978), pages 344–346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

In one aspect of the present invention, the sulfur vulcanizable rubber composition is then sulfur-cured or vulcanized.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, preferably about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The mixing of the rubber composition can be accomplished by methods known to those having skill in the rubber mixing art. For example the ingredients are typically mixed in at least two stages, namely at least one non-productive stage followed by a productive mix stage. The final curatives including sulfur vulcanizing agents are typically mixed in the final stage which is conventionally called the "productive" mix stage in which the mixing typically occurs at a temperature, or ultimate temperature, lower than the mix temperature(s) than the preceding non-productive mix stage (s). The rubber, filler, siloxy compound of Formula I and carbon black, if used, are mixed in one or more non-productive mix stages. The terms "non-productive" and "productive" mix stages are well known to those having skill in the rubber mixing art. The sulfur vulcanizable rubber composition containing the salt of Formula I, vulcanizable rubber and generally at least part of the silica should be subjected to a thermomechanical mixing step. A sulfur containing organosilicon compound of Formula IV may be present. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions and the volume and nature of the components. For example, the thermomechanical working may be from 1 to 20 minutes.

In further accordance with the invention, the process comprises the additional step of vulcanizing the prepared rubber composition at a temperature in a range of about 140° C. to about 190° C.

Accordingly, the invention also thereby contemplates a vulcanized rubber composition prepared by such process.

In additional accordance with the invention, the process comprises the additional steps of preparing an assembly of a tire or sulfur-vulcanizable rubber with a tread comprised of the said rubber composition prepared according to the process of this invention and vulcanizing the assembly at a temperature in a range of about 140° C. to about 190° C.

Accordingly, the invention also thereby contemplates a vulcanized tire prepared by such process.

Vulcanization of the rubber composition of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

Upon vulcanization of the sulfur vulcanized composition, the rubber composition of this invention can be used for various purposes. For example, the sulfur vulcanized rubber composition may be in the form of a tire, belt or hose. In case of a tire, it can be used for various tire components. Such tires can be built, shaped, molded and cured by various methods which are known and will be readily apparent to those having skill in such art. Preferably, the rubber composition is used in the tread of a tire. As can be appreciated, the tire may be a passenger tire, aircraft tire, truck tire and the like. Preferably, the tire is a passenger tire. The tire may also be a radial or bias, with a radial tire being preferred.

EXAMPLE I

Preparation of 3-Ammonium-Propyl-Triethoxysilane-Propyl-Triethoxysilane-Silane-Sulfide-3

44.27 g (0.2 mole) of 3-aminopropyltriethoxysilane and 47.68 g (0.2 mole) 3-polyethylene bottle was closed and the ingredient were mixed. The polyethylene bottle was kept at 70° C. for 12 hours (one night in drying oven).

The formation of the desired product was confirmed by NMR by the disappearance of the two amino- and the one mercapto-proton signal and the appearance of a one peak corresponding to three equivalent protons as postulated. The reaction was highly quantitative because no specific amino and mercapto proton peak could be detected.

EXAMPLE II

Table 1 below shows the ingredients of four rubber compounds. Control Sample A contained no silane compound. Sample B contained the aminosilane of formula III. Sample C contained the mercaptosilane of formula II. All parts and percentages were by weight unless otherwise noted. All samples were prepared with the same procedure and ingredients except as to the use of the respective amount (phr) of ingredients listed in Table 1. The cure data as well as other physical data for each sample are listed in Table 2.

TABLE 1

| Material | Parts Sample A | Parts Sample B | Parts Sample C | Parts Sample D |
| --- | --- | --- | --- | --- |
| Non-Productive | | | | |
| IBR[1] | 42 | 42 | 42 | 42 |
| E-SBR[2] | 31.62 | 31.62 | 31.62 | 31.62 |
| PBD[3] | 25 | 25 | 25 | 25 |

TABLE 1-continued

| Material | Parts Sample A | Parts Sample B | Parts Sample C | Parts Sample D |
| --- | --- | --- | --- | --- |
| Natural rubber | 10 | 10 | 10 | 10 |
| Z1165MP[4] | 83 | 83 | 83 | 83 |
| 3-aminopropyl triethoxysilane[5] | 0 | 6.64 | 0 | 0 |
| 3-mercaptopropyl triethoxysilane[6] | 0 | 0 | 6.64 | 0 |
| Reaction product of Example 1[7] | 0 | 0 | 0 | 6.64 |
| Carbon black, N330 | 6.64 | 6.64 | 6.64 | 6.64 |
| Processing oil | 15 | 15 | 15 | 15 |
| Antiozonant | 2.25 | 2.25 | 2.25 | 2.25 |
| Waxes | 1.5 | 1.5 | 1.5 | 1.5 |
| Productive | | | | |
| Antioxidant | 1 | 1 | 1 | 1 |
| Zinc oxide | 2.5 | 2.5 | 2.5 | 2.5 |
| Fatty acid | 3 | 3 | 3 | 3 |
| Sulfur | 1.95 | 1.95 | 1.95 | 1.95 |
| Accelerators | 1.6 | 1.6 | 1.6 | 1.6 |

[1]Isoprene/butadiene copolymer rubber having an isoprene content of about 50% by weight obtained from The Goodyear Tire & Rubber Company and a Tg of about −45° C.
[2]Emulsion polymerized SBR having a styrene content of about 41%, 37.5 phr of oil and of the type obtainable as 1712 from the Huels AG Company.
[3]Cis 1,4-polybutadiene rubber obtained as Budene ™ 1207 from the Goodyear Tire & Rubber Company
[4]High reinforcing grade silica sold by Rhodia under the designation Z1165MP
[5]3-aminopropyltriethoxysilane obtained from ABCR GMBH and Co., Box 21 01 35 D-76151, Karlsruhe, Germany in Gelest catalogue No. SIA0610.0.
[6]3-mercaptopropyltriethoxysilane obtained from ABCR GMBH and Co., P.O. 21 01 35 D-76151, Karlsruhe, Germany in Gelest catalogue No. SIM6475.0
[7]Reaction product of Example 1, 3-ammonium-propyl-triethoxysilane-propyl-triethoxysilane-sulfide-3

TABLE 2

| Material | Parts Sample A | Parts Sample B | Parts Sample C | Parts Sample D |
| --- | --- | --- | --- | --- |
| Rheometer (160° C.) | | | | |
| % 25 (min) | 1.7 | 0.43 | 1.44 | 0.79 |
| T50 (min) | 2.72 | 1.3 | 3 | 1.3 |
| T90 (min) | 11 | 7.53 | 13.84 | 8.65 |
| Delta Torque (dNm) | 28.7 | 28.4 | 10.7 | 11.1 |
| Rheometer (190° C.) T-1 (min) | 5 | 00[8] | 00[8] | 00[8] |
| Mooney Plasticity ML (1 + 10) | 85 | 85 | 65.4 | 53.7 |
| Tensile Properties | | | | |
| Tensile strength (MPa) | 13.7 | 16.1 | 13 | 16 |
| Elongation at break (%) | 736 | 605 | 389.5 | 453 |
| Specific energy | 40 | 38 | 19 | 21 |
| 100% Modulus (MPa) | 1.4 | 1.7 | 2 | 1.7 |
| 200% Modulus (MPa) | 2.5 | 3.5 | 5.1 | 4.1 |
| 300% Modulus (MPa) | 4.3 | 6.7 | 10.1 | 9 |
| Modulus Ratio[9] | 3 | 3.9 | 5 | 5.3 |
| Shore A | 69 | 76.1 | 61.7 | 58.3 |
| Rebounds | | | | |
| 23° C. (%) | 37.8 | 37 | 44.1 | 42.9 |
| 100° C. (%) | 52 | 49.4 | 61.7 | 62.1 |
| Delta Rebound (%) | 14.2 | 12.4 | 17.6 | 19.2 |
| Dynamic Mechanical Properties | | | | |
| Tan Delta at 50° C. | 0.167 | 0.171 | 0.148 | 0.149 |
| Tan Delta at 0° C. | 1.296 | 20.25 | 0.3 | 0.3 |
| Tan Delta at −20° C. | 0.636 | 0.491 | 0.644 | 0.644 |

TABLE 2-continued

| Material | Parts Sample A | Parts Sample B | Parts Sample C | Parts Sample D |
|---|---|---|---|---|
| DIN Abrasion Volume loss (cm³) | 196 | 141 | 80 | 85 |

[8]00 = Marching modulus
[9]Modulus ratio = Modulus 300% Modulus 100%

Discussion

The above data for Sample D demonstrate the benefit of a high reversion stability characterized by an infinite T-1 at 190° C. vs. 5 minutes for the Sample A, an acceptable t90 at 150° C. of 8 minutes for Sample A and B and a low delta torque vs. Sample A and B. The data for Example D exhibits a lower Mooney plasticity compared to Sample A, B and C, which is a prerequisite for good processability (extrusion). The data also shows advantages for Sample D of a low rolling resistance characterized by a high hot rebound vs. Sample A and B; a high reinforcement characterized by a high modulus 300% vs. Sample A and B combined with a high Tensile strength compared to Sample A and C; a high potential for wet skid/Rolling resistance trade off characterized by a beneficial delta rebound differential versus Sample A, B and C and lower tan delta at 50 versus Sample A and B and higher tan delta at −20° C. versus Sample A and B.

In addition, the data for Sample D shows a high potential for tread wear indicated by a high modulus ratio of comparative Sample D versus A, B and C and particularly by the DIN abrasion volume loss of comparative sample D versus Sample A and B.

While certain representative embodiments and details have been shown for the purpose of illustrating the invention, it will be apparent to those skilled in this art that various changes and modifications may be made therein without departing from the spirit or scope of the invention.

What is claimed is:

1. A method of processing a rubber composition which comprises mixing:
   (i) 100 parts by weight of at least one sulfur vulcanizable elastomer containing olefinic unsaturation;
   (ii) 10 to 250 phr of a filler selected from the group consisting of particulate precipitated silica, aluminosilicates, carbon black, modified carbon black and mixtures thereof; and
   (iii) 0.05 to 15 phr of a siloxy compound of the formula:

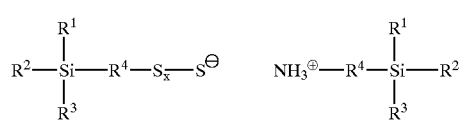
I wherein each $R^1$ and $R^1$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes and alkyl substituted arylenes having from 6 to 10 carbon atoms, $-R^5-O-R^6-$ and $-R^5-NH-R^7-$; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and X is an integer of from 0 to 7.

2. The method of claim 1 wherein said filler is particulate precipitated silica.

3. The method of claim 1 wherein each $R^1$, $R^2$ and $R^3$ is an alkoxy radical having 1 to 3 carbon atoms, each $R^4$ is an alkylene group having 1 to 3 carbon atoms; and x is 0.

4. The method of claim 1 wherein said siloxy compound is added in an amount ranging from 0.10 to 10.0 phr.

5. The method of claim 1 wherein a symmetrical sulfur containing organosilicon compound is present and is of the formula:

$$Z\text{-Alk-}S_n\text{-Alk-}Z \qquad \qquad IV$$

in which Z is selected from the group consisting of:

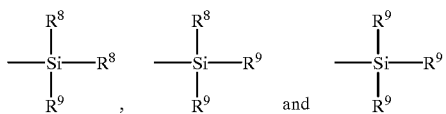

where $R^8$ is an alkyl group of 1 to 4 carbon atoms, cyclohexyl or phenyl; $R^9$ is alkoxy of 1 to 8 carbon atoms, or cycloalkoxy of 5 to 8 carbon atoms; Alk is a divalent hydrocarbon of 1 to 18 carbon atoms and n is an integer of 2 to 8.

6. The method of claim 1 wherein said sulfur vulcanizable elastomer containing olefinic unsaturation is selected from the group consisting of natural rubber, neoprene, polyisoprene, butyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM silicon-coupled star-branched polymers, tin-coupled star-branched polymers and mixtures thereof.

7. The method of claim 1 wherein said rubber composition is thermomechanically mixed at a rubber temperature in a range of from 140° C. to 190° C. for a mixing time of from 1 to 20 minutes.

8. A rubber composition comprising:
   (i) an elastomer containing olefinic unsaturation;
   (ii) 10 to 250 phr of a filler selected from the group consisting of particulate precipitated silica, aluminosilicates, carbon black, modified carbon black and mixtures thereof; and
   (iii) 0.05 to 15 phr of a siloxy compound of the formula:

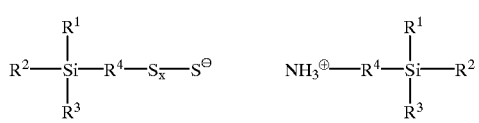
I wherein each $R^1$ and $R^2$ are independently selected from the group consisting of alkoxy radicals having from 1 to 8 carbon atoms and alkyls having from 1 to 8 carbon atoms; $R^3$ is selected from the group consisting of alkoxy radicals having from 1 to 8 carbon atoms; each $R^4$ is independently selected from the group consisting of alkylenes and having from 1 to 15 carbon atoms, arylenes and alkyl substituted arylenes having from 6 to 10 carbon atoms, $-R^5-O-$ $R^6$— and —$R^5$—NH—$R^7$—; $R^5$ and $R^7$ are independently selected from the group consisting of alkylenes having from 1 to 15 carbon atoms, arylenes and alkyl substituted arylenes having from 6 to 10 carbon atoms; $R^6$ is selected from the group consisting of alkylenes having from 1 to 15 carbon atoms, arylenes and alkyl substituted arylenes having from 6 to 10 carbon atoms and alkenylenes having from 2 to 15 carbon atoms; and x is an integer of from 0 to 7.

9. The composition of claim 8 wherein each $R^1$, $R^2$ and $R^3$ is an alkoxy radical having 1 to 3 carbon atoms; each $R^4$ is an alkylene group having 1 to 3 carbon atoms; and x is 0.

10. The composition of claim 8 wherein said siloxy compound is present in an amount ranging from 0.10 to 10 phr.

11. The composition of claim 8 wherein a symmetrical sulfur containing organosilicon compound is present and is of the formula:

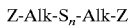

in which Z is selected from the group consisting of:

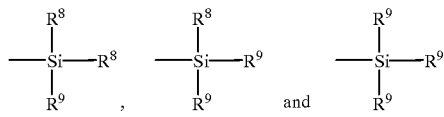

where $R^6$ is an alkyl group of 1 to 4 carbon atoms, cyclohexyl or phenyl; $R^7$ is alkoxy of 1 to 8 carbon atoms, or cycloalkoxy of 5 to 8 carbon atoms; Alk is a divalent hydrocarbon of 1 to 18 carbon atoms and n is an integer of 2 to 8.

12. The composition of claim 8 wherein said filler is particulate precipitated silica.

13. The composition of claim 8 wherein said elastomer containing olefinic unsaturation is selected from the group consisting of natural rubber, neoprene, polyisoprene, butyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM silicon-coupled star-branched polymers, tin-coupled star-branched polymers and mixtures thereof.

14. The composition of claim 8 wherein said composition was thermomechanically mixed at a rubber temperature in a range of from 140° C. to 190° C. for a total mixing time of from 1 to 20 minutes.

15. A sulfur vulcanized rubber composition which is prepared by heating the composition of claim 8 to a temperature ranging from 100° C. to 200° C. in the presence of a sulfur vulcanizing agent.

16. The sulfur vulcanized rubber composition of claim 15 in the form of a tire, belt or hose.

* * * * *

UNITED STATES PATENT AND TRADEMARK OFFICE
CERTIFICATE OF CORRECTION

PATENT NO. : 6,593,433 B2
DATED : July 15, 2003
INVENTOR(S) : Giorgio Agostini

It is certified that error appears in the above-identified patent and that said Letters Patent is hereby corrected as shown below:

Column 11,
Lines 37-40, delete the entire paragraph starting with "44.27 g" and insert therefor
-- 44.27g (0.2 mole) of 3-aminopropyltriethoxysilane and 47.68 g(o.2 mole) 3-mercoptopropyltriethoxysilane were charged to a 250 ml polyethylene bottle. The polyethylene bottle was closed and the ingredients were mixed. The polyethylene bottle was kept at 70°C for 12 hours (one night in drying oven). --

Signed and Sealed this

Twenty-fourth Day of August, 2004

JON W. DUDAS
*Director of the United States Patent and Trademark Office*